United States Patent
Nordstrom (10) Patent No.: US 9,730,599 B2
(45) Date of Patent: *Aug. 15, 2017

(54) TELEMETRICALLY ENHANCED ATHLETIC APPAREL

(71) Applicant: NIKE, Inc., Beaverton, OR (US)

(72) Inventor: Matthew D. Nordstrom, Portland, OR (US)

(73) Assignee: NIKE, Inc., Beaverton, OR (US)

(*) Notice: Subject to any disclaimer, the term of this patent is extended or adjusted under 35 U.S.C. 154(b) by 0 days.

This patent is subject to a terminal disclaimer.

(21) Appl. No.: 15/201,894

(22) Filed: Jul. 5, 2016

(65) Prior Publication Data

US 2016/0309801 A1    Oct. 27, 2016

Related U.S. Application Data

(63) Continuation of application No. 13/828,893, filed on Mar. 14, 2013, now Pat. No. 9,402,429.

(51) Int. Cl.
| | |
|---|---|
| *A61B 5/0408* | (2006.01) |
| *A61B 5/00* | (2006.01) |
| *A41D 13/12* | (2006.01) |
| *A41B 1/08* | (2006.01) |
| *A41D 1/00* | (2006.01) |

(Continued)

(52) U.S. Cl.
CPC .......... *A61B 5/04085* (2013.01); *A41B 1/08* (2013.01); *A41D 1/002* (2013.01);
(Continued)

(58) Field of Classification Search
CPC ... A61B 5/0006; A61B 5/0024; A61B 5/0408; A61B 5/04085; A61B 5/6804; A61B 5/6805; A61D 13/12814
See application file for complete search history.

(56) References Cited

U.S. PATENT DOCUMENTS

| | | |
|---|---|---|
| 5,610,877 A | 3/1997 | Adams et al. |
| 6,895,261 B1 | 5/2005 | Palamides |
| | (Continued) | |

FOREIGN PATENT DOCUMENTS

| | | |
|---|---|---|
| EP | 2505090 A2 | 10/2012 |
| WO | 0101855 A1 | 1/2001 |
| WO | 2012113014 A1 | 8/2012 |

OTHER PUBLICATIONS

European Search Report dated Sep. 29, 2016 in European Patent Application No. 14774013.8, 8 pages.

*Primary Examiner* — Lee S Cohen
(74) *Attorney, Agent, or Firm* — Shook, Hardy & Bacon L.L.P.

(57) ABSTRACT

A telemetrically enhanced article of clothing comprises a fabric layer having an inside surface and an outside surface. A sensor is attached to the inside surface of the fabric layer such that when the article of clothing is worn by the user, the sensor is in contact with the user's skin. An electrically conductive trace may extend along the fabric layer and may be electrically connected at a first end to the sensor. A retaining ring may be adhered to the fabric layer near a second end of the electrically conductive trace. The retaining ring is capable of receiving a telemetry device and forming a compression connection between the perimeter of the telemetry device and the retaining ring such that when the telemetry device is received in the retaining ring, the second end of the electrically conductive trace is in electrical contact with the telemetry device. The telemetry device may store, process, or transmit physiological and/or other data collected by a sensor.

10 Claims, 7 Drawing Sheets

(51) Int. Cl.
  *A44B 17/00* (2006.01)
  *A63B 24/00* (2006.01)
  *A63B 71/06* (2006.01)

(52) U.S. Cl.
  CPC ...... *A41D 13/1281* (2013.01); *A44B 17/0076* (2013.01); *A61B 5/0006* (2013.01); *A61B 5/0024* (2013.01); *A61B 5/0408* (2013.01); *A61B 5/6804* (2013.01); *A63B 24/0062* (2013.01); *A63B 71/0686* (2013.01); *A61B 2503/10* (2013.01); *A61B 2562/225* (2013.01); *A63B 2220/20* (2013.01); *A63B 2220/62* (2013.01); *A63B 2230/06* (2013.01)

(56) References Cited

U.S. PATENT DOCUMENTS

| | | | |
|---|---|---|---|
| 7,124,447 | B2 | 10/2006 | Arganese |
| 7,324,841 | B2 | 1/2008 | Reho et al. |
| 7,684,755 | B2 | 3/2010 | Pierce et al. |
| 7,793,361 | B2 | 9/2010 | Ishihara et al. |
| 8,032,199 | B2 | 10/2011 | Linti et al. |
| 8,340,740 | B2 | 12/2012 | Holzer et al. |
| 8,386,009 | B2 | 2/2013 | Lindberg et al. |
| 8,750,959 | B2 | 6/2014 | Lindberg et al. |
| 8,909,318 | B2 | 12/2014 | Nordstrom |
| 9,402,429 | B2 * | 8/2016 | Nordstrom ......... A41D 13/1281 |
| 2005/0217005 | A1 | 10/2005 | DeSantis |
| 2006/0196093 | A1 | 9/2006 | Krauss |
| 2007/0250981 | A1 | 11/2007 | Seibert |
| 2008/0096726 | A1 | 4/2008 | Riley et al. |
| 2008/0125288 | A1 | 5/2008 | Case |
| 2009/0204013 | A1 | 8/2009 | Muhlsteff et al. |
| 2010/0185398 | A1 | 7/2010 | Berns et al. |
| 2010/0198043 | A1 | 8/2010 | Holzer et al. |
| 2010/0234715 | A1 | 9/2010 | Shin et al. |
| 2012/0165645 | A1 | 6/2012 | Russell et al. |
| 2012/0238910 | A1 | 9/2012 | Nordstrom |

* cited by examiner

FIG. 12

TELEMETRICALLY ENHANCED ATHLETIC APPAREL

CROSS-REFERENCE TO RELATED APPLICATIONS

This application entitled "Telemetrically Enhanced Athletic Apparel," is a continuation application of U.S. application Ser. No. 13/828,893, filed Mar. 14, 2013, now U.S. Pat. No. 9,402,429, and entitled "Telemetrically Enhanced Athletic Apparel." The entirety of the aforementioned application is incorporated by reference herein.

STATEMENT REGARDING FEDERALLY SPONSORED RESEARCH OR DEVELOPMENT

Not applicable.

TECHNICAL FIELD

The present invention relates to athletic apparel. More particularly, the present invention relates to articles of clothing capable of receiving telemetry devices and exercise telemetry kits.

BACKGROUND

In the modern information age, both professional and amateur athletes are increasingly interested in quantifying their performance. Various existing devices such as GPS-enabled watches or microchips implanted in shoes measure stride, distance traveled, pace, and other aspects of a user's performance. Other devices measure physiological aspects of a user's performance, such as heart rate. Conventional systems for gathering user performance data, however, are often inconvenient, cumbersome, or difficult to implement. For example, heart rate monitors provide a user with heart rate information, but the user must endure the inconvenience and discomfort of wearing a chest strap and monitoring device.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

An article of clothing is provided. The article of clothing comprises a fabric layer having an inside surface and an outside surface. The inside surface faces a user's body when the article of clothing is worn by the user, and the outside surface faces away from the user's body when the article of clothing is worn by the user. A sensor is attached to the inside surface of the fabric layer such that when the article of clothing is worn by the user, the sensor is in contact with the user's skin. The sensor is capable of measuring physiological parameters of the user. An electrically conductive trace extends along the fabric layer and is electrically connected at a first end to the sensor. An elastic retaining ring is adhered to the fabric layer near a second end of the electrically conductive trace. The retaining ring is capable of receiving a rounded telemetry device and forming a compression connection between the perimeter of the telemetry device and the retaining ring such that when the telemetry device is received in the retaining ring, the second end of the electrically conductive trace is in electrical contact with the telemetry device.

BRIEF DESCRIPTION OF THE DRAWINGS

The present invention is described in detail below with reference to the attached drawing figures, wherein.

DETAILED DESCRIPTION

Conventional systems for gathering user performance data are often inconvenient and cumbersome. The present invention provides articles of clothing capable of receiving a telemetry device, the articles of clothing allowing convenient gathering and storage and/or transmission of user performance data. A retaining ring receives and secures the telemetry device to the article of clothing. Sensors in contact with the user's skin and traces extending between the sensors and the retaining ring are integrated into the article of clothing to provide the received telemetry device with physiological user performance data. The traces are brought into electrical contact with the telemetry device when the device is received in the retaining ring. Data can be stored locally in the telemetry device while the user is exercising and can be subsequently uploaded for analysis. Data can also be transmitted wirelessly from the telemetry device to a second device for storage and/or analysis. Examples of the present invention are illustrated in FIGS. 1-12.

Figure 1:
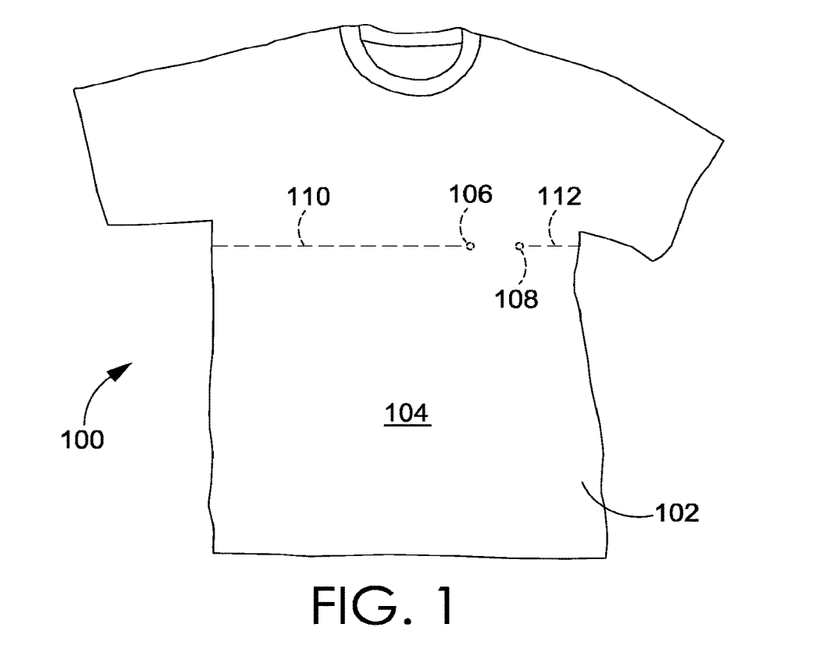
FIG. 1 is a perspective view of the back of an exemplary telemetrically enhanced shirt in accordance with an example of the present invention.

FIG. 1 illustrates a shirt 100. Shirt 100 is an article of clothing capable of receiving a telemetry device. FIG. 1 illustrates front portion 102 of shirt 100. Shirt 100 comprises a fabric layer 104. Fabric layer 104 has an inside surface (not shown) and an outside surface (visible in FIG. 1). The inside surface faces a user's body when the shirt is worn by the user, and the outside surface faces away from the user's body when the shirt is worn by the user. Sensors 106 and 108 are attached to the inside surface of fabric layer 104 such that when shirt 100 is worn by a user, sensors 106 and 108 are in contact with the user's skin. Sensors 106 and 108 are capable of measuring physiological parameters of the user. In one example, sensors 106 and 108 are capable of measuring heart rate. Sensors 106 and 108 can be any of a number of known sensor types. Shirt 100 may be designed to be form fitting such that sensors 106 and 108 remain in contact with the user's skin while shirt 100 is worn.

Two electrically conductive traces 110 and 112 extend along fabric layer 104. Trace 110 is connected at a first end to sensor 106, and trace 112 is connected at a first end to sensor 108. As shown in FIG. 1 using dotted lines, traces 110 and 112 extend along the inside surface of fabric layer 104. In some examples, either or both of traces 110 and 112 cross through from the inside surface of fabric layer 104 to the outside surface of fabric layer 104 and extend along the outside surface of fabric layer 104. In other examples, all or some traces may be replaced with radio frequency or other wireless signal transmission technologies.

Figure 2:
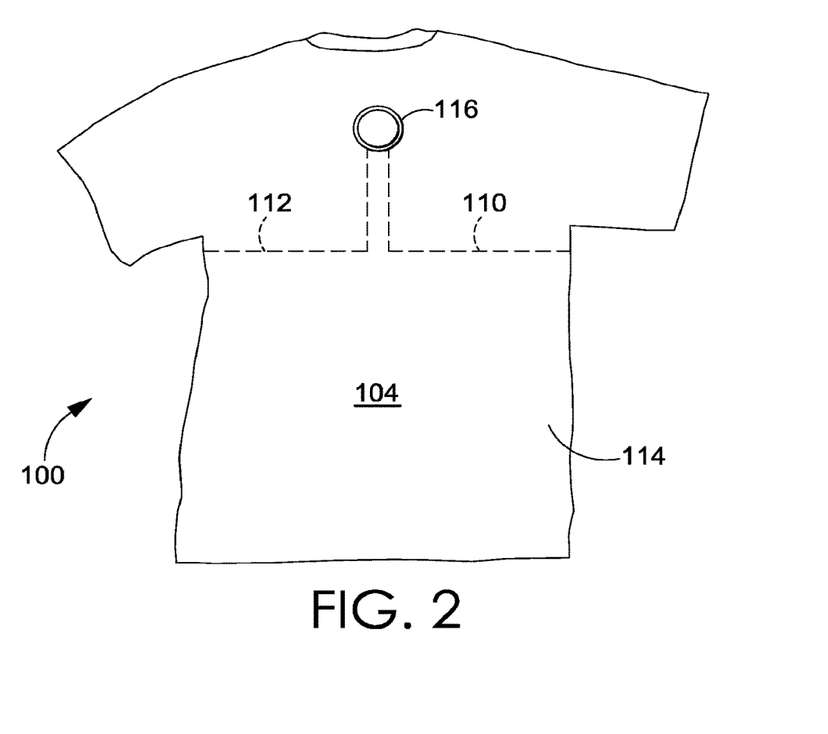
FIG. 2 is a perspective view of the front of an exemplary telemetrically enhanced shirt in accordance with an example of the present invention.

FIG. 2 illustrates back portion 114 of shirt 100. Electrically conductive traces 110 and 112 extend along the inside surface of fabric layer 104 from sensors 106 and 108 in FIG. 1, around to back portion 114, and up to elastic retaining ring 116 in FIG. 2. Retaining ring 116, which may also be referred to as a bezel, may be adhered to fabric layer 104 near a second end of electrically conductive traces 110 and 112. The shape of retaining ring 116 may be selected to correspond to a telemetry device, and need not be circular in all examples of apparel in accordance with the present invention. Retaining ring 116 is capable of receiving a telemetry device and forming a compression connection between the perimeter of the telemetry device and retaining ring 116 such that when the telemetry device is received in retaining ring 116, the second ends of electrically conductive traces 110 and 112 are in electrical contact with the telemetry device. Thus, a runner, for example, can simply pull on shirt 100, insert a telemetry device into retaining ring 116, and conveniently begin her run while user performance data, such as physiological data, is measured by sensors 106 and 108 and transmitted through traces 110 and 112 to a received telemetry device.

Although a shirt is illustrated in FIGS. 1 and 2, examples of the invention include a variety of articles of clothing, including clothing designed for specifically for men or women. Additionally, it should be understood that the location of sensors 106 and 108 and traces 110 and 112 in FIG. 1 are exemplary. A variety of sensor placements and trace routing patterns are contemplated. In one example, a women's shirt is designed such that sensors and/or traces are placed to accommodate a sports bra or other support garment underneath the shirt. Elastic retaining ring 116 can be adhered at a variety of locations on shirt 100, and any number of sensors and traces are contemplated. In the example shown in FIG. 2, retaining ring 116 is adhered to fabric layer 104 in an area corresponding to the upper back between a user's shoulder blades. In some examples, retaining ring 116 is adhered to the outside surface of fabric layer 104 as shown in FIG. 2. Any other location may be selected for a retaining ring on a garment in accordance with the present invention. In other examples, retaining ring 116 is adhered to the inside surface of fabric layer 104.

Figure 3A:
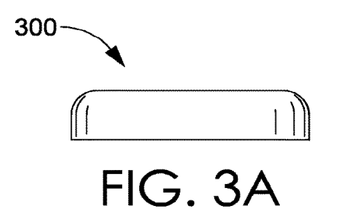
FIG. 3A is a side perspective view of a telemetry device receivable by an exemplary article of clothing in accordance with an example of the present invention.
Figure 3B:
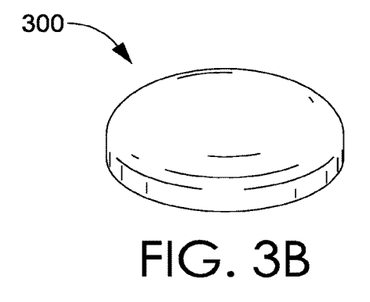
FIG. 3B is a perspective view of the telemetry device of FIG. 3B.

FIGS. 3A-5 illustrate exemplary telemetry devices that can be inserted into an article of clothing in accordance with the present invention. FIG. 3A is a side perspective view of telemetry device 300 receivable by an exemplary article of clothing in accordance with an example of the present invention. FIG. 3B shows an additional perspective view of telemetry device 300 of FIG. 3A. Telemetry device 300 has a substantially circular footprint. Other telemetry devices having different footprints are contemplated.

Figure 4:
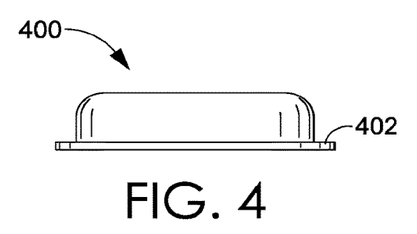
FIG. 4 is a side perspective view of a telemetry device receivable by an exemplary article of clothing in accordance with an example of the present invention, the telemetry device having a lip.

FIG. 4 is a side perspective view of a telemetry device 400 receivable by an exemplary article of clothing in accordance with an example of the present invention. Telemetry device 400 may have a lip 402 around the perimeter of device 400. Lip 402 acts to provide additional force to secure telemetry device 400 in a retaining ring and to "snap" the device 400 into place, as is illustrated below in FIGS. 8A-8C. Lip 402 may also be referred to as a flange or other terms. Lip 402 may be constructed of the same or different material than the body of telemetry device 400. The thickness and width of lip 402 may vary based upon the properties of the materials used and/or the stresses expected to be applied to telemetry device 400.

Figure 5:
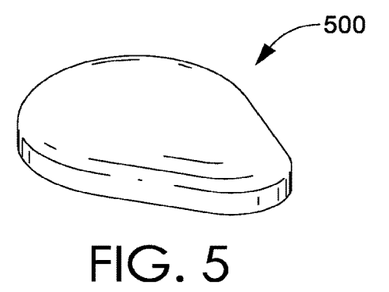
FIG. 5 is a perspective view of a telemetry device receivable by an exemplary article of clothing in accordance with an example of the present invention, the telemetry device being narrower at one end than the other.

FIG. 5 is a perspective view of telemetry device 500. In contrast to telemetry device 300 of FIGS. 3A and 3B, telemetry device 500 has a footprint resembling a simplified ice cream cone, with a rounded triangular portion combined with a semi-circle. Such a footprint allows a user to immediately identify the orientation of device 500 visually and/or tactilely, because one end is narrower than the other. The example shape illustrated in FIG. 5 comprises only one example of a large number of potential shapes of a telemetry device that may provide an inherent alignment indication. Telemetry devices may have other geometries that allow quick identification of orientation. The user is then able to insert telemetry device 500 in the proper orientation into a retaining ring such as retaining ring 116 in FIG. 2 to ensure electrical contact is made between device 500 and electrically conductive traces such as traces 110 and 112 in FIGS. 1 and 2.

As used in this application, a "telemetry device" is a device capable of storing and/or relaying user performance data including physiological data such as heart rate and non-physiological data such as pace, time, and distance traveled. A telemetry device may simply store data until a user decides to upload the data to a computing device. Alternatively or additionally, a telemetry device may include a wireless transmitter for transmitting received data to a second device or external storage unit. A telemetry device may additionally make measurements, for example by containing a GPS receiver and measuring distance traveled. In one example, a telemetry device receivable by an article of clothing in accordance with the present invention includes at least one electrical contact. The at least one electrical contact makes an electrical connection with at least one electrically conductive trace in the article of clothing, thereby allowing the telemetry device to receive signals from sensors connected to the at least one trace. "Telemetrically enhanced" is used in this application to describe an article of clothing with the ability to receive a telemetry device and bring the received device into electrical contact with one or more sensors. Telemetry devices in accordance with the present invention may also have various displays, indicators, lights, etc., that may be used to indicate the status of the device, such as on/off, or to output information gathered by the device.

Figure 6:
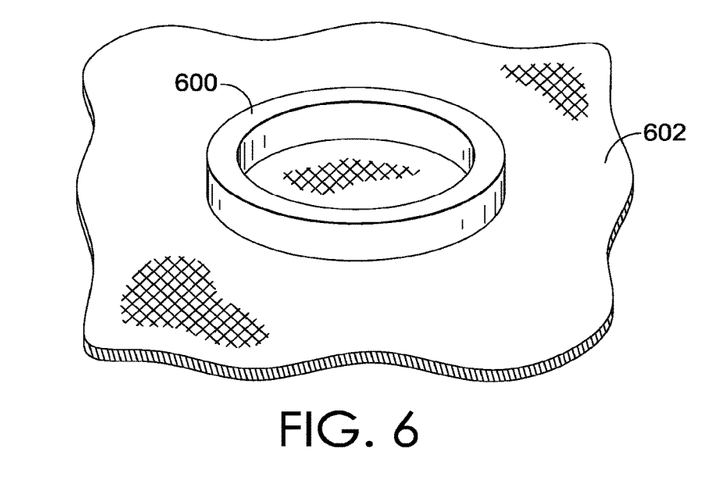
FIG. 6 is a perspective view of an exemplary retaining ring adhered to an exemplary fabric layer in accordance with an example of the present invention.

FIG. 6 is a perspective view of an exemplary retaining ring 600 adhered to an exemplary fabric layer 602. Retaining ring 600 may be elastic, thereby permitting a telemetry device to be easily inserted into and secured by retaining ring 600. In some examples, retaining ring 600 is substantially made of silicone, and it is the elastic properties of silicone that allow easy insertion and securing of a telemetry device. Alternatively/additionally, the textile used in constructing apparel in accordance with the present invention may have sufficient elasticity to permit a telemetry device to be inserted into even a relatively rigid retaining ring. The size of a retaining ring may vary based, for example, on its material and location. For example, a silicone retaining ring may be approximately one sixteenth of an inch thick.

Figure 7A:
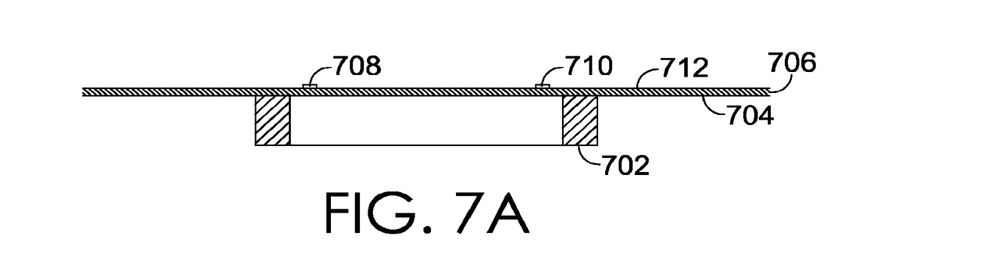
FIG. 7A is a cross-sectional view of an exemplary retaining ring and fabric layer in accordance with an example of the present invention.
Figure 7B:
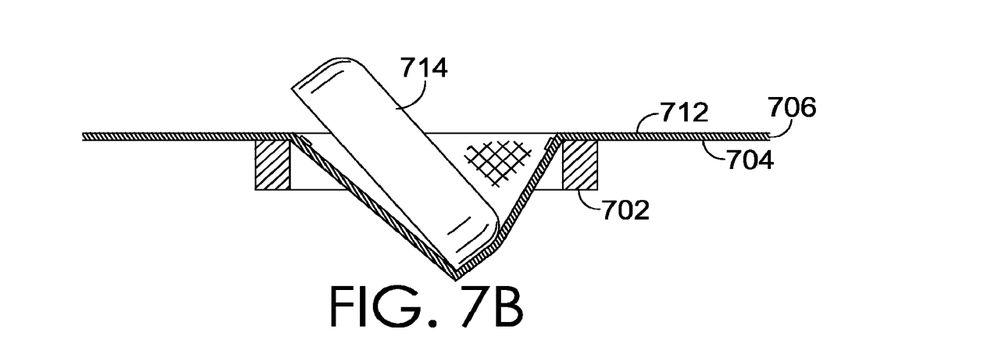
FIG. 7B is a cross-sectional view of the exemplary retaining ring and fabric layer of FIG. 7A in which the exemplary telemetry device shown in FIG. 3 has been partially inserted.
Figure 7C:
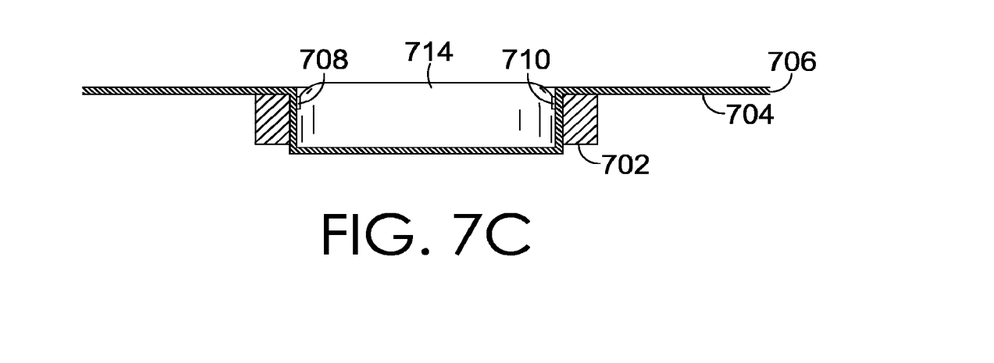
FIG. 7C is a cross-sectional view of the exemplary retaining ring and fabric layer of FIG. 7A in which the exemplary telemetry device shown in FIG. 3 is received.

FIGS. 7A-7C, 8A-8C, 9A-9C, and 10A-10C illustrate in detail examples of how a telemetry device is inserted into retaining rings adhered to either the inside surface or outside surface of a fabric layer. Similarly, a telemetry device may be inserted from either the inside or outside of a garment, regardless as to which side of the fabric layer a retaining ring is located. FIGS. 7A-7C illustrate an example in which elastic retaining ring 702 is adhered to the interior surface 704 of fabric layer 706 and electrically conductive trace ends 708 and 710 are on the outside surface 712 of fabric layer 706. Trace ends 708 and 710 are inside the area bounded by retaining ring 702. The traces for which ends 708 and 710 are shown are connected at their other ends to sensors attached to inside surface 704. Thus, at some point in the path from the sensors to retaining ring 702, the traces were brought through the article of clothing to outside surface 712 of fabric layer 704. In some examples, the traces are brought through fabric layer 704 to one surface or the other as needed for the particular design. The traces may be brought through fabric layer 704 by a variety of methods, including integrating the traces in the weaving or knitting of fabric layer 704 in such a way that the traces switch from one surface to the other through the weave or knit of fabric layer 704; running the traces through a hole in fabric layer 704; or through other methods.

FIG. 7B illustrates insertion of a telemetry device 714 into retaining ring 702. In this example, telemetry device 714 is inserted from outside surface 712 of fabric layer 704 because this will make possible an electrical connection between trace ends 708 and 710, which are on outside surface 712. FIG. C illustrates telemetry device 714 being received in retaining ring 702. When telemetry device 714 is received in retaining ring 702, telemetry device 714 is in contact with outside surface 712 of fabric layer 704 and a portion of fabric layer 704 is between retaining ring 702 and received telemetry device 714. Thus, while a compression connection is formed between the perimeter of telemetry device 714 and retaining ring 702 in this example, telemetry device 714 is not in direct contact with retaining ring 702. In the examples shown in this application, the electrical contact areas of telemetry device 714 are not shown. A variety of placements and sizes of contact areas are contemplated.

Thus, in the example illustrated in FIGS. 7A-7C, retaining ring 702 is on the inside of a user's article of clothing, and telemetry device 714 is inserted from the outside of the user's clothing. In addition to providing a mechanical connection that secures telemetry device 714 to the article of clothing, the compression connection between the perimeter of telemetry device 714 and retaining ring 702 maintains the electrical connection between trace ends 708 and 712 and telemetry device 714. Maintaining the electrical connection through compression eliminates the need for a cumbersome socket-type electrical connector.

Figure 8A:
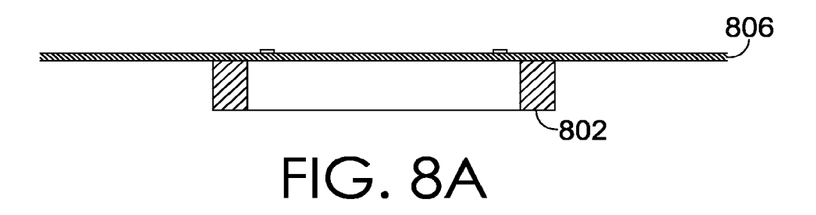
FIG. 8A is a cross-sectional view of an exemplary retaining ring and fabric layer in accordance with an example of the present invention.
Figure 8B:
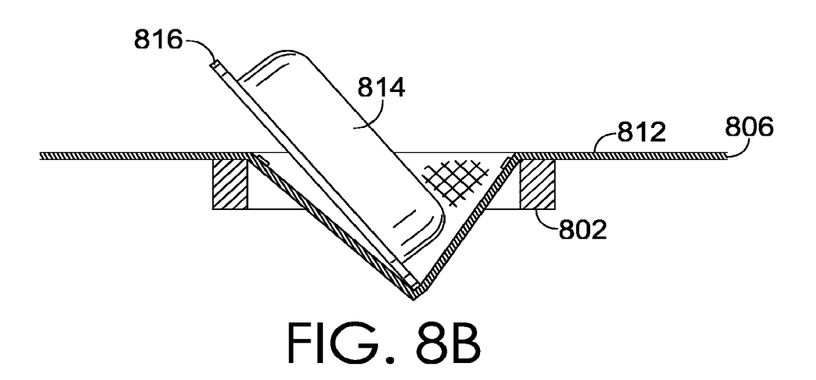
FIG. 8B is a cross-sectional view of the exemplary retaining ring and fabric layer of FIG. 8A in which the exemplary telemetry device shown in FIG. 4 has been partially inserted.
Figure 8C:
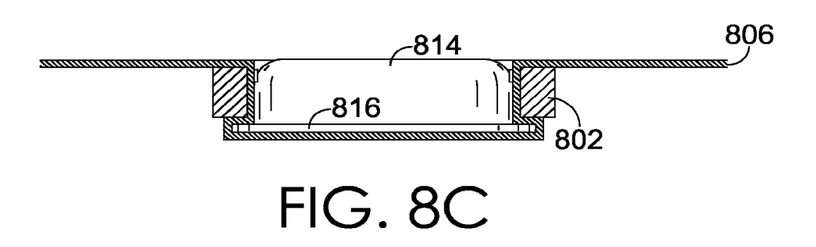
FIG. 8C is a cross-sectional view of the exemplary retaining ring and fabric layer of FIG. 8A in which the exemplary telemetry device shown in FIG. 4 is received.
Figure 9A:
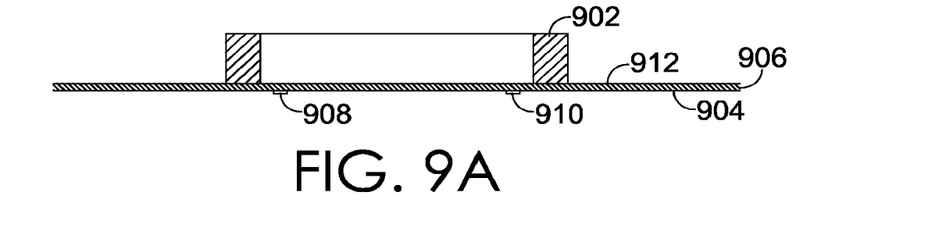
FIG. 9A is a cross-sectional view of an exemplary retaining ring and fabric layer in accordance with an example of the present invention.
Figure 9B:
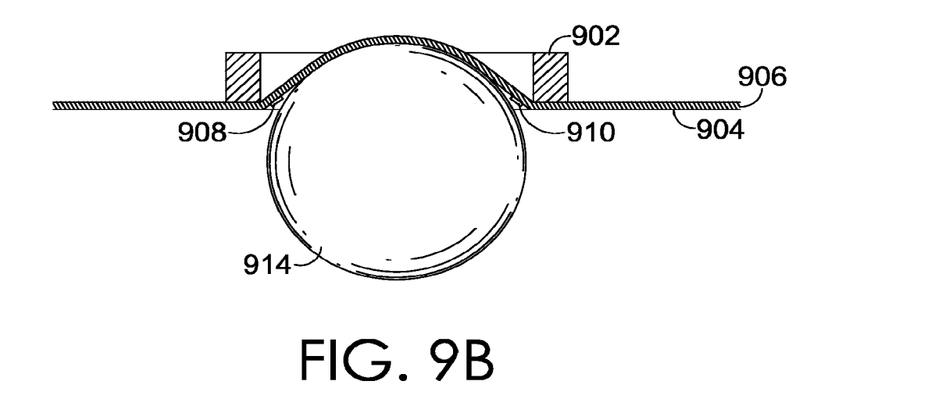
FIG. 9B is a cross-sectional view of the exemplary retaining ring and fabric layer of FIG. 9A in which the exemplary telemetry device shown in FIG. 3 has been partially inserted.
Figure 9C:
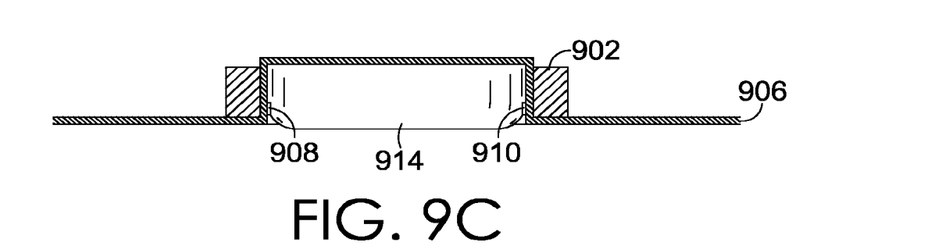
FIG. 9C is a cross-sectional view of the exemplary retaining ring and fabric layer of FIG. 9A in which the exemplary telemetry device shown in FIG. 3 is received.
Figure 10A:
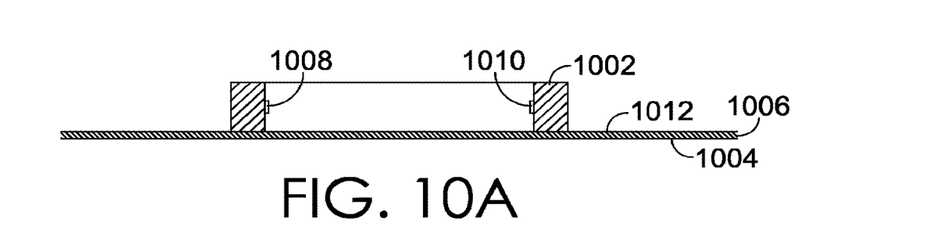
FIG. 10A is a cross-sectional view of an exemplary retaining ring and fabric layer in accordance with an example of the present invention.
Figure 10B:
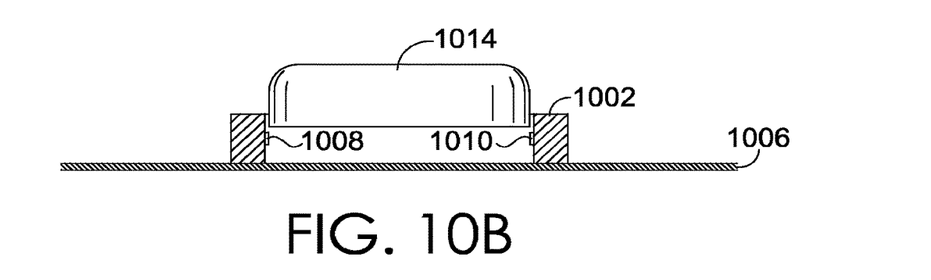
FIG. 10B is a cross-sectional view of the exemplary retaining ring and fabric layer of FIG. 10A in which the exemplary telemetry device shown in FIG. 3 has been partially inserted.
Figure 10C:
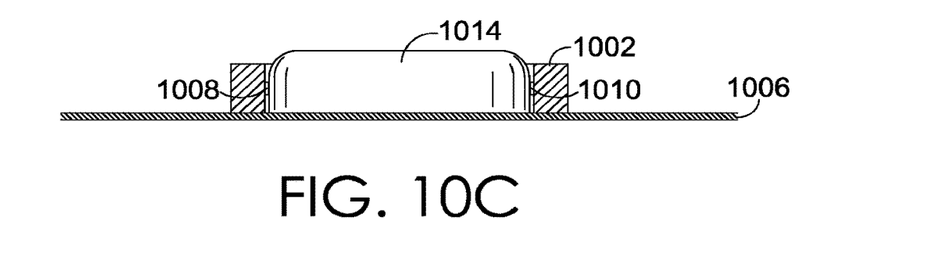
FIG. 10C is a cross-sectional view of the exemplary retaining ring and fabric layer of FIG. 10A in which the exemplary telemetry device shown in FIG. 3 is received.

FIGS. 8A-8C illustrate another example where a retaining ring is on the inside of the article of clothing, and the telemetry device is inserted from the outside of the clothing. FIGS. 9A-9C illustrate an example where the retaining ring is on the outside of the article of clothing, and the telemetry device is inserted from the inside of the clothing. FIGS. 10A-10C illustrate an example where the retaining ring is on the outside of the article of clothing and the telemetry device is also inserted from the outside of the article of clothing.

FIGS. 8A-8C illustrate an example similar to that illustrated in FIGS. 7A-7C except that received telemetry device 814 has a lip 816 around the perimeter. Lip 816 provides an additional force to secure telemetry device 814 in retaining ring 802, as illustrated in FIG. 8C. When telemetry device 814 is received as shown in FIGS. 8B and 8C such that lip 816 is pushed through retaining ring 802 from the outside surface 812 of fabric layer 806, lip 816 presses back against retaining ring 802 with a force in the opposite direction from the direction in which telemetry device 814 was inserted, securing telemetry device 814 in retaining ring 802. Additionally, retaining ring 802 exerts a compressive force around the perimeter of telemetry device 814 as illustrated in FIGS. 7A-7C.

In FIGS. 9A-9C, retaining ring 902 is adhered to the outside surface 912 of fabric layer 906, and telemetry device 914 is inserted from the inside of the clothing. Electrically conductive trace ends 908 and 910 are on the inside surface 904 of fabric layer 906. When telemetry device 914 is received in retaining ring 902 as shown in FIG. 9C, telemetry device 914 is in contact with inside surface 904 of fabric layer 906 and a portion of fabric layer 906 is between retaining ring 902 and received telemetry device 914.

FIGS. 10A-10C show an example in which retaining ring 1002 is adhered to outside surface 1012 of fabric layer 1006. Electrically conductive trace ends 1008 and 1010 are attached to the interior perimeter of retaining ring 1002. In some examples, at least a portion of the interior perimeter of retaining ring 1002 is conductive and is electrically connected to trace ends 1008 and 1010. When telemetry device 1014 is received in retaining ring 1002, telemetry device 1014 is in direct contact with retaining ring 1002, and trace ends 1008 and 1010 are in electrical contact with telemetry device 1014. In one example, electrically conductive trace ends 1008 and 1010 are on outside surface 1012 of fabric layer 1006. In another example in which the retaining ring is adhered to the outside surface (not shown), the trace ends are on the inside surface of the fabric layer. In this example, when the telemetry device is received in the retaining ring, the telemetry device is in contact with the inside surface of the fabric layer and a portion of the fabric layer is between the retaining ring and the received telemetry device.

Figure 11:
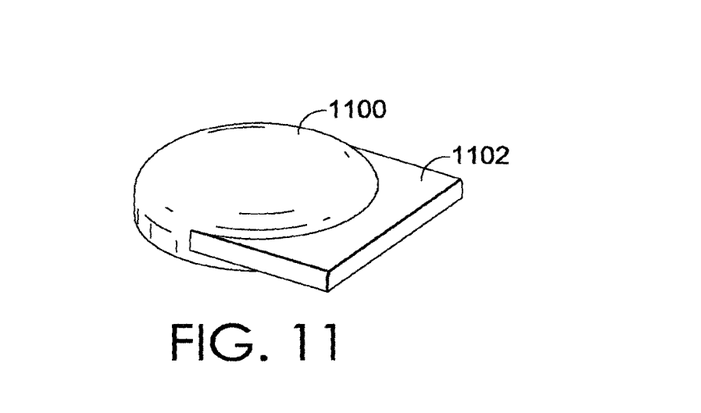
FIG. 11 is a side perspective view of a telemetry device receivable by an exemplary article of clothing in accordance with an example of the present invention, the telemetry device having a protrusion for ease of insertion and alignment.

FIG. 11 is a side perspective view of another exemplary telemetry device 1100 receivable by a telemetrically enhanced article of clothing in accordance with an example of the present invention. Telemetry device 1100 has a protrusion 1102 for ease of insertion and alignment. In some examples, a telemetrically enhanced article of clothing is designed such that when protrusion 1102 is oriented in a specific way and/or aligned with a marking or indicator, telemetry device 1100 makes electrical connection with trace ends of traces connected to sensors attached to the interior surface of the article of clothing. Thus, protrusion 1102 acts as an alignment mechanism and as a convenient handhold for inserting and removing telemetry device 1100. It is contemplated that protrusion 1102 can be configured in a number of ways and that multiple protrusions may be included in any particular telemetry device.

Figure 12:
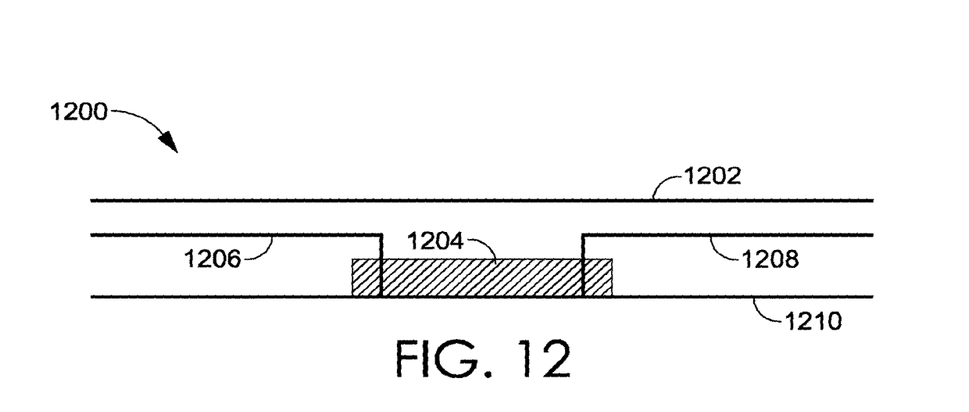
FIG. 12 is an exaggerated plan view of an exemplary thermal appliqué including a retaining ring and electrically conductive traces in accordance with an example of the present invention.

In another example, a retaining ring, trace ends, and/or electrically conductive traces may be incorporated together and attached to the fabric layer of an article of clothing using a heat transfer process. An exaggerated plan view of such a heat transfer 1200 is illustrated in FIG. 12. Heat transfer 1200 includes an adhesive layer 1202 that is applied against a fabric layer. Heat transfer 1200 may have a retaining ring 1204 and electrically conductive traces 1206 and 1208. In some examples, retaining ring 1204 is composed substantially of silicone and is electrically conductive. Heat transfer 1200 also includes carrier sheet 1210. When heat transfer 1200 of FIG. 12 may be applied to an article of clothing, for example, on the outside surface of the fabric layer, and a telemetry device may be received from the outside surface. Similarly, a heat transfer 1200 may be applied to the inside surface of an article of clothing, and a telemetry device is received from the inside surface. The space that receives a telemetry device may comprise an opening left during the creation of a heat transfer or may comprise a structural portion of a heat transfer.

In yet another example, the trace ends are substantially larger than the traces themselves such that precise placement of the telemetry device is not required to bring the trace ends into electrical contact with the telemetry device. In another example, the electrical contacts on the telemetry device are large so that precise placement of the telemetry device is not required.

In still another example, an exercise telemetry kit is contemplated including a telemetrically enhanced article of clothing as described in any of the examples discussed above, such as a form-fitting shirt, and a rounded telemetry device having at least one electrical contact for receiving data and one of a wireless transmitter or memory.

The present invention has been described in relation to particular examples, which are intended in all respects to be illustrative rather than restrictive. Alternative examples will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated by and is within the scope of the claims.

Having thus described the invention, what is claimed is:

1. An article of clothing comprising:
    a fabric layer having an inside surface and an outside surface, the inside surface facing a user's body when the article of clothing is worn by the user, and the outside surface facing away from the user's body when the article of clothing is worn by the user;
    a sensor attached to the inside surface of the fabric layer;
    at least one electrically conductive trace extending along the fabric layer and electrically connected at a first end to the sensor; and
    a retaining bezel secured at least to the inside surface of the fabric layer near a second end of the electrically conductive trace, the retaining bezel capable of receiving a device and forming a connection between the device and the retaining bezel such that when the device is received in the retaining bezel, the second end of the electrically conductive trace is in electrical contact with the device.

2. The article of clothing of claim 1, wherein the second end of the electrically conductive trace is on the outside surface of the fabric layer, and wherein when the device is received in the retaining bezel, the device is in contact with the outside surface of the fabric layer and a portion of the fabric layer is between the retaining bezel and the received device.

3. The article of clothing of claim 1, wherein the second end of the electrically conductive trace is at least partially inside an area bounded by the retaining bezel.

4. The article of clothing of claim 1, wherein the retaining bezel has an interior perimeter, and wherein at least a portion of the interior perimeter is conductive and is electrically connected to the second end of the electrically conductive trace.

5. The article of clothing of claim 1, wherein a shape of the retaining bezel corresponds to a shape of the device.

6. The article of clothing of claim 1, further comprising:
    an additional sensor attached to the inside surface of the fabric layer; and
    an additional electrically conductive trace extending along the fabric layer and electrically connected at a first end to the additional sensor, wherein a second end of the additional electrically conductive trace is located near the retaining bezel, and wherein when the device is received in the retaining bezel, the second end of the additional electrically conductive trace is in electrical contact with the device.

7. An article of clothing comprising:
    a fabric layer having an inside surface and an outside surface, the inside surface facing a user's body when the article of clothing is worn by the user, and the outside surface facing away from the user's body when the article of clothing is worn by the user;

at least two sensors attached to the inside surface of the fabric layer;

two electrically conductive traces extending along the fabric layer, each trace electrically connected at a first end to one of the two sensors; and a retaining bezel adhered to the inside surface of the fabric layer near a second end of each of the electrically conductive traces, the retaining bezel capable of receiving a device and forming a connection between the perimeter of the device and the retaining bezel such that when the device is received in the retaining bezel, the second ends of the two electrically conductive traces are in electrical contact with the device.

8. The article of clothing of claim 7, wherein the second end of each of the electrically conductive traces is on the outside surface of the fabric layer, and wherein when the device is received in the retaining bezel, the device is in contact with the outside surface of the fabric layer and a portion of the fabric layer is between the retaining bezel and the received device.

9. The article of clothing of claim 7, wherein the article of clothing in in the form of a shirt.

10. An exercise telemetry kit comprising:

a device having two electrical contacts for receiving data and one of a wireless transmitter or memory; and an article of clothing comprising:

a fabric layer having an inside surface and an outside surface, the inside surface facing a user's body when the article of clothing is worn by the user, and the outside surface facing away from the user's body when the article of clothing is worn by the user;

at least one sensor attached to the inside surface of the fabric layer;

two electrically conductive traces extending along the fabric layer, each trace electrically connected at a first end to the one sensor; and a retaining bezel adhered to the inside surface of the fabric layer near a second end of each of the electrically conductive traces, the retaining bezel capable of receiving the device and forming a connection between the perimeter of the device and the retaining bezel such that when the device is received in the retaining bezel, the second ends of the two electrically conductive traces are in electrical contact with the two electrical contacts of the device.

\* \* \* \* \*

UNITED STATES PATENT AND TRADEMARK OFFICE
CERTIFICATE OF CORRECTION

PATENT NO.         : 9,730,599 B2
APPLICATION NO.    : 15/201894
DATED              : August 15, 2017
INVENTOR(S)        : Matthew D. Nordstrom Page 1 of 1

It is certified that error appears in the above-identified patent and that said Letters Patent is hereby corrected as shown below:

In the Claims

Column 9, Line 24: Please remove "in in" and replace with --is in--.

Signed and Sealed this
Tenth Day of October, 2017

Joseph Matal
*Performing the Functions and Duties of the*
*Under Secretary of Commerce for Intellectual Property and*
*Director of the United States Patent and Trademark Office*